(12) United States Patent
Rusek et al.

(10) Patent No.: US 8,049,048 B2
(45) Date of Patent: *Nov. 1, 2011

(54) RENEWABLE ENGINE FUEL

(75) Inventors: John J Rusek, West Lafayette, IN (US); Mary-Louise R Rusek, West Lafayette, IN (US); Jonathon D Ziulkowski, West Lafayette, IN (US)

(73) Assignee: Swift Enterprises, Ltd. IN (US)

( * ) Notice: Subject to any disclaimer, the term of this patent is extended or adjusted under 35 U.S.C. 154(b) by 457 days.

This patent is subject to a terminal disclaimer.

(21) Appl. No.: 12/139,428

(22) Filed: Jun. 13, 2008

(65) Prior Publication Data

US 2008/0244961 A1    Oct. 9, 2008

Related U.S. Application Data

(63) Continuation-in-part of application No. 11/881,565, filed on Jul. 27, 2007, now abandoned.

(60) Provisional application No. 60/833,589, filed on Jul. 27, 2006.

(51) Int. Cl.
C07C 7/20    (2006.01)

(52) U.S. Cl. .......................................... 585/1

(58) Field of Classification Search ............... 585/1, 14
See application file for complete search history.

(56) References Cited

U.S. PATENT DOCUMENTS

| | | | | | |
|---|---|---|---|---|---|
| 2,401,983 | A | * | 6/1946 | Stanly et al. | 585/14 |
| 2,593,561 | A | * | 4/1952 | Herbst et al. | 44/454 |
| 6,353,143 | B1 | * | 3/2002 | Fang et al. | 585/1 |

OTHER PUBLICATIONS

Roubaud et al, Oxidation and Combustion of Low Alkylbenzenes at High Pressure, 2000, Combustion and Flame 121:535-541.*

* cited by examiner

*Primary Examiner* — Cephia D Toomer
(74) *Attorney, Agent, or Firm* — Townsend & Banta

(57) ABSTRACT

The present invention provides fully renewable engine fuels derived completely from biomass sources. In one embodiment the fully renewable engine fuel is comprised of one or more low carbon number esters, one or more pentosan-derivable furans, one or more aromatic hydrocarbon, one or more $C_4$-$C_{10}$ straight chain alkanes derivable from polysaccharides, and one or more bio-oils. In addition, the fuel may contain triethanolamine. Such a lower octane renewable fuel may be utilized, for example, in automobile fuel, 100 LL aviation fuel applications, and turbine engine applications. These ethanol-based, fully renewable fuels may be formulated to have a wide range of octane values and energy, and may effectively be used to replace 100 LL aviation fuel (known as AvGas), as well as high octane, rocket, diesel, and turbine engine fuels. In another embodiment, there is provided a synthetic high octane aviation fuel comprising isopentane and mesitylene, and process of producing same from a biomass.

1 Claim, 2 Drawing Sheets

RENEWABLE ENGINE FUEL

This is a continuation-in-part application of non-provisional U.S. patent application Ser. No. 11/881,565, filed Jul. 27, 2007, now abandoned which claims priority of provisional U.S. patent application Ser. No. 60/833,589, filed Jul. 27, 2006.

FIELD OF THE INVENTION

The present invention relates in general to an engine fuel produced from renewable materials and, in particular, the present invention provides a non-petroleum based fuel produced fully from renewable materials. In one embodiment, one of the fuels of the present invention may be formulated into a variety of octane ratings, including a high octane rating used in aviation fuels, as well as lower octane ratings utilized in automobile and truck applications. Further, the components that make the effective renewable fuel can be mixed to form jet turbine and diesel fuels. In another embodiment, the present invention provides synthetic 100 octane aviation fuels comprising binary mixtures of compounds derived from a biomass.

BACKGROUND OF THE INVENTION

With the end of cheap oil and the mounting peak of world oil production, it is recognized that petroleum is a non-renewable resource and will eventually be depleted. This realization has sparked a renewed interest in the development of renewable sources for fuel. This is particularly true in the case of aviation fuels used in internal combustion engines, as well as for jet fuels.

In the United States, the Federal Aviation Administration (FAA) is responsible for setting the technical standards for aviation fuels. Currently, the FAA uses as a standard for aviation fuel the 100 LL aviation gasoline. To qualify as a 100 octane aviation fuel, any new fuel must comply with the current aviation gasoline specification ASTM D910. This is true whether the new fuel is based on petroleum or a chemical or chemical combination.

Ethanol-based fuels for internal combustion engines have been available for roughly five decades. The State of California originated mandatory oxygenation of motor fuels, which includes ethanol-based fuels, partly to decrease the wholesale cost of fuel, and to a lesser extent to reduce air pollution per gallon of gasoline consumed. Effectively, since ethanol-based fuels have lower energy, pollution is generally increased per mile. A key benefit of ethanol-based fuels is that they have a slightly higher octane number than ethanol-free gasoline. This is the reason many oil companies provide high ethanol containing premium fuels and lower ethanol regular grades of gasoline. Renewable fuels made from some chemical species other than ethanol have been found to exhibit significantly higher octane numbers and increased energy per unit volume when compared to commercial fuels and ethanol-based fuels.

Octane (Power)

Octane number is a measure of the effectiveness of power production. It is a kinetic parameter, therefore difficult to predict. Oil companies compiled volumes of experimental octane data (for most hydrocarbons) for the Department of Defense in the 1950's. The method used to obtain this dynamic parameter is discussed in the next paragraph. 2,2,4-trimethyl pentane (isooctane) has a defined octane number of 100, and n-heptane has a defined octane number of 0, based on experimental tests. Octane numbers are linearly interpolated and extrapolated by this method, hence predictions for mixes can be made once pure sample values are determined.

Automobile gasoline is placarded at the pump as the average of Research and Motor octane numbers. These correlate to running a laboratory test engine (CFR) under less severe and more severe conditions, respectively. True octane numbers lie between the Research and Motor octane values. Aviation fuel has a "hard" requirement of 100 MON (motor octane number); ethanol has a MON of 96, which makes its use only viable when mixed with other higher octane components. Conventional 100 LL (i.e., 100 octane low lead) contains about 3 ml of tetraethyl lead per gallon.

Range (Energy)

The inherent energy contained within gasoline is directly related to mileage, not to octane number. Automobile gasoline has no energy specification, hence no mileage specification. In contrast, aviation fuels, a common example being 100 LL (100 octane low lead), have an energy content specification. This translates to aircraft range and to specific fuel consumption. In the octane examples above, i-octane and n-heptane had values of 100 and 0, respectively. From an energy perspective, they contain heat of combustion values of 7.84 and 7.86 kcal/ml, respectively, which is the reverse of what one would expect based on power developed. Aircraft cannot compromise range due to the sensitivity of their missions. For this reason, energy content is equally important as MON values.

The current production volume of 100 LL is approximately 850,000 gallons per day. 100 LL has been designated by the Environmental Protection Agency (EPA) as the last fuel in the United States to contain tetraethyl lead. This exemption will likely come to an end in the near future (2010).

Although a number of chemical compounds have been found to satisfy the motor octane number for 100 LL octane aviation fuel, they fail to meet a number of other technical requirements for aviation fuel. This is true, for example, for isopentane, 90 MON, and trimethyl benzene 136 MON.

Pure isopentane fails to qualify as an aviation fuel because it does not pass the ASTM specification D909 for supercharge ON, ASTM specification D2700 for motor octane number, and ASTM specification D5191 for vapor pressure.

Pure sym-trimethyl benzene (mesitylene) also fails to qualify as an aviation fuel because it does not pass ASTM specification D2386 for freeze point, ASTM specification D5191 for vapor pressure, and ASTM specification D86 for the 10% distillation point. Table 3 herein shows these test results and the ASTM standard for both isopentane and trimethyl benzene.

The fermentation of a biomass using microbes to produce acetone and butanol was first discovered by Chaim Weizmann in 1916 and is described in U.S. Pat. No. 1,315,585 and other corresponding patents throughout the world. This process known as the Weizmann process was used by both Great Britain and the United States in World Wars I and II to produce acetone for the production of cordite used in making smokeless powder.

A number of methods are known for making mesitylene from acetone and include, for example:

liquid phase condensation in the presence of strong acids, e.g. sulfuric acid and phosphoric acid as described in U.S. Pat. No. 3,267,165 (1966);

vapor phase condensation with tantalum containing catalysts as described in U.S. Pat. No. 2,917,561 (1959);

vapor phase condensation using as catalyst the phosphates of the metals of group IV of the periodic system of elements, e.g. titanium, zirconium, hafnium and tin as described in U.S. Pat. No. 3,94,079 (1976);

vapor phase reaction in the presence of molecular hydrogen and a catalyst selected from alumina containing chromia and boria as described in U.S. Pat. No. 3,201,485 (1965);

vapor phase reaction using catalysts containing molybdenum as described in U.S. Pat. No. 3,301,912 (1967) or tungsten as described in U.S. Pat. No. 2,425,096, a vapor phase reaction over a niobium supported catalyst with high selectivity. The catalyst is preferably made by impregnating a silica support with an ethanolic solution of $NCl_5$ or an aqueous solution of Nb in order to deposit 2% Nb by weight and by calcining the final solid at 550° C. for 18 hours. At 300° C., the condensation of acetone produces mainly mesitylene (70% selectivity) at high conversion (60-80% wt) as described in U.S. Pat. No. 5,087,781.

It is also known in the art to dimerize acetone to form isopentane. This process involves first dimerizing acetone to form diacetone alcohol which is then dehydrated to form mesitytl oxide. The mesityl oxide then undergoes gas phase reformation hydrogenation to form isopentane.

It is an object of the present invention to provide renewable fuels that effectively replaces 100 LL aviation gasoline with an unleaded, fully renewable alternative.

It is another object of the present invention to provide fully renewable fuels for other internal combustion/heat engines as well.

It is a further object of the present invention to provide high energy renewable fuels for use in turbines and other heat engines by the same methodology; the energy content and physical properties of the renewable components being tailored to the type of engine to be fueled.

It is another object of the present invention to provide a binary mixture of components which meet the technical specifications for aviation fuel of 100 LL octane.

It is another object of the present invention to provide a non-petroleum based aviation fuel of 100 LL octane which meets the technical specifications of the Federal Aviation Administration for 100 LL octane petroleum-based aviation fuels.

It is still another object of the present invention to provide a process for the production from a biomass of the components of a binary chemical mixture which satisfies the technical specifications for 100 LL octane aviation fuel.

It is yet another object of the present invention to provide a process for the production of a new chemical based 100 LL octane aviation fuel from renewable sources.

SUMMARY OF THE INVENTION

In order to achieve the objects of the present invention, the present inventors have arduously carried out research and endeavored to provide a fully renewable fuel, preferably derived from biomass, having a high octane and a high energy content. Accordingly, in a first embodiment of the present invention, the present inventors provide a renewable fuel comprised of:
  (a) one or more low carbon esters derivable from ethanol;
  (b) one or more pentosan derivable furans;
  (c) one or more aromatic hydrocarbons derived from acetone or propyne;
  (d) one or more $C_4$-$C_{10}$ straight chain alkanes derivable from polysaccharides; and
  (e) one or more bio-oils derived from plant germ.

In a second embodiment of the present invention, the renewable fuel of the first embodiment above is provided, wherein:
  (a) the low carbon esters derivable from ethanol are present in an amount of from about greater than 0 to 20 wt %, based on the total weight of the fuel.
  (b) the pentosan derivable furans are present in an amount of from about greater than 0 to 20 wt %, based on the total weight of the fuel;
  (c) the aromatic hydrocarbon derived from acetone or propyne are present in an amount of from about greater than 0 to 60 wt %, based on the total weight of the fuel;
  (d) the one or more $C_4$-$C_{10}$ straight chain alkanes derivable from polysaccharides are present in an amount of from about greater than 0 to 65 wt %, based on the total weight of the fuel
  (e) the bio-oils derived from plant germ are present in an amount of from about 2 to 40 wt %, based on the total weight of the fuel.

In a third embodiment of the present invention, the renewable fuel of the first embodiment above is provided, wherein the low carbon esters derived from ethanol are esters having a carbon number of $C_1$ to $C_4$.

In a fourth embodiment of the present invention, the renewable fuel of the first embodiment above is provided, wherein the low carbon ester derived from ethanol is ethyl acetate.

In a fifth embodiment of the present invention, the renewable fuel of the first embodiment above is provided, wherein the pentosan derivable furans are substituted furans.

In a sixth embodiment of the present invention, the renewable fuel of the first embodiment above is provided, wherein the pentosan derivable furan is 2-methyl furan.

In a seventh embodiment of the present invention, the renewable fuel of the first embodiment above is provided, wherein the aromatic hydrocarbon is mesitylene.

In an eighth embodiment of the present invention, the renewable fuel of the first embodiment above is provided, wherein the one or more $C_4$-$C_{10}$ straight chain alkanes derivable from polysaccharides are one or more selected from the group consisting of n-butane through n-decane.

In a ninth embodiment of the present invention, the renewable fuel of the first embodiment above is provided, wherein the one or more $C_4$-$C_{10}$ straight chain alkanes derivable from polysaccharides. Preferably, the straight chain alkanes are one or more of n-pentane, n-hexane, n-heptane, n-octane, and n-nonane.

In a tenth embodiment of the present invention, the renewable fuel of the first embodiment above is provided, wherein the $C_4$-$C_{10}$ straight chain alkanes are n-heptane.

In an eleventh embodiment of the present invention, the renewable fuel of the first embodiment above is provided, wherein the $C_4$-$C_{10}$ straight chain alkanes are an equal molar volume mixture of n-hexane and n-octane.

In a twelfth embodiment of the present invention, the renewable fuel of the first embodiment above is provided, wherein the bio-oils derived from plant germ are one or more selected from the group consisting of soybean oil, rapeseed oil, canola oil, palm oil, algae oil and corn oil.

In a thirteenth embodiment of the present invention, the renewable fuel of the first embodiment of the present invention above is provided, wherein the bio-oil derived from plant germ is corn oil.

In a fourteenth embodiment of the present invention, the renewable fuel of the first embodiment above further comprises (f) triethanolamine.

In a fifteenth embodiment of the present invention, the renewable fuel of the fourteenth embodiment above is provided, wherein the fuel comprises from about greater than 0 to about 10 wt % of triethanolamine.

In a sixteenth embodiment of the present invention, the present inventors discovered a renewable fuel comprised of a binary mixture of components derived from a biomass, which provides an effective synthetic aviation fuel meeting the requirements of the Federal Aviation Administration.

In a seventeenth embodiment of the present invention, the present inventors discovered a synthetic high octane aviation fuel comprising:
(a) at least one aromatic hydrocarbon, and
(b) at least one isoparaffin having from 4 to 6 carbon atoms.

In an eighteenth embodiment of the present invention, the present inventors discovered the synthetic high octane aviation fuel of the seventeenth embodiment, wherein the aromatic hydrocarbon is present in an amount of at least about 60 wt %; and the isoparaffin is present in an amount of at least about 15 wt %.

In a nineteenth embodiment of the present invention, the present inventors discovered the high synthetic octane aviation fuel of the seventeenth embodiment, wherein the aromatic hydrocarbon is present in an amount of no more than about 85 wt %; and the isoparaffin is present in an amount of no more than about 40 wt %.

In a twentieth embodiment of the present invention, the present inventors discovered the synthetic high octane aviation fuel of the seventeenth embodiment, wherein the aromatic hydrocarbon is sym-trimethyl benzene (mesitylene).

In a twenty-first embodiment of the present invention, the present inventors discovered the synthetic high octane aviation fuel of the twentieth embodiment, which further comprises a normally liquid isoparaffin.

In a twenty-second embodiment of the present invention, the present inventors discovered the synthetic high octane aviation fuel of the twentieth embodiment, wherein the mesitylene is present in an amount of no more than about 85 wt %.

In a twenty-third embodiment of the present invention, the present inventors discovered the synthetic high octane aviation fuel of the twenty-first embodiment, wherein the normally liquid isoparaffin is isopentane.

In a twenty-fourth embodiment of the present invention, the present inventors discovered the synthetic high octane aviation fuel of the twentieth embodiment, wherein the mesitylene is present in an amount of at least about 70 wt %.

In a twenty-fifth embodiment of the present invention, the present inventors discovered the synthetic high octane aviation fuel of the twenty-third embodiment, wherein the isopentane is present in an amount of at least 15 wt %.

In a twenty-sixth embodiment of the present invention, the present inventors discovered the synthetic high octane aviation fuel of the twentieth embodiment, wherein the mesitylene is present in an amount of between about 70 to 85 wt %.

In a twenty-seventh embodiment of the present invention, the present inventors discovered the synthetic high octane aviation fuel of the twenty-third embodiment, wherein the isopentane is present in an amount of between about 15 to 30 wt %.

In a twenty-eighth embodiment of the present invention, the present inventors discovered a process for the production of synthetic aviation fuel from a biomass, comprising the steps of:
(a) fermenting a biomass using a microorganism of clostridium acetolbutylicum or a mutagen thereof to produce a mixture of metabolites comprising acetone and butanol;
(b) separating the acetone from butanol and any ethanol in the mixture by fractional distillation;
(c) dimerizing a portion of resultant acetone to form isopentane;
(d) trimerizing another portion of the resultant acetone to form mesitylene; and
(e) mixing the isopentane with mesitylene from steps (c) and (d) whereby to form synthetic high octane aviation fuel.

In a twenty-ninth embodiment of the present invention, the present inventors discovered the process of the twenty-eighth embodiment, wherein the biomass is selected from the group consisting of sugars, celluloses, lignins, starches, and lignocelluloses.

In a thirtieth embodiment of the present invention, the present inventors discovered the process of the twenty-eighth embodiment, wherein the biomass is selected from the group consisting of hard woods, grasses, corn stover, sorghum, corn fiber, and oat hulls, which are pretreated with enzymes or strong acids to break hemicellulose chains into their sugar monomers.

In a thirty-first embodiment of the present invention, the present inventors discovered the twenty-eighth embodiment, wherein the fermentation in step (a) is conducted in an anaerobic reactor in the absence of oxygen.

In a thirty-second embodiment of the present invention, the present inventors discovered the process of the twenty-eighth embodiment, wherein metabolites of acetone, butanol and ethanol from step (a) are stripped from the fermentation when concentrations thereof over 2 to 3 wt % are obtained, whereby to avoid poisoning of the organism clostridium acetolbutylicum or mutagens thereof.

In a thirty-third embodiment of the present invention, the present inventors discovered the process of the twenty-eighth embodiment, wherein the trimerizing of acetone in step (d) is carried out in the gas phase by reacting acetone with sulfuric or phosphoric acid at elevated temperatures.

In a thirty-fourth embodiment of the present invention, the present inventors discovered the process of the twenty-eighth embodiment, wherein the dimerization of acetone in step (c) is carried out in a catalytic reaction to yield isopentane.

In a thirty-fifth embodiment of the present invention, the present inventors discovered the process of the twenty-eighth embodiment, wherein the dimerization of acetone in step (c) is carried out in a gas phase catalytic reaction.

In a thirty-sixth embodiment of the present invention, the present inventors discovered the process of the twenty-eighth embodiment, wherein the trimerizing of acetone in step (d) is carried out in the presence of a catalyst.

DETAILED DESCRIPTION OF THE INVENTION

Figure 1:
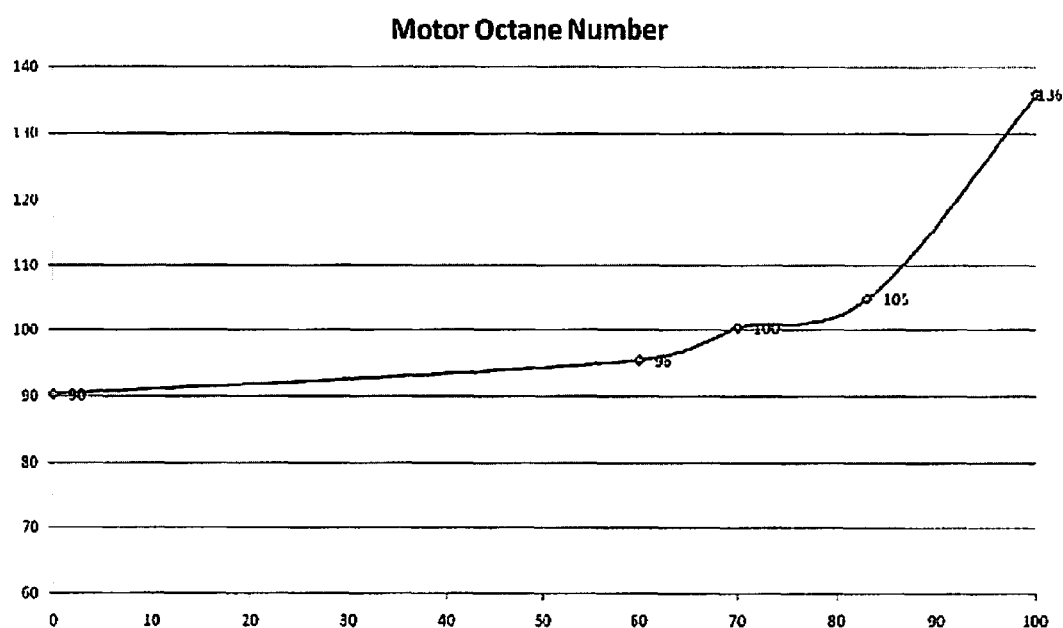
FIG. 1 is a graph of the motor octane number as a function of wt % of mesitylene for the binary mixture of isopentane and mesitylene of the present invention.

As discussed above, the present invention provides a non-petroleum-based renewable fuel comprised of fully renewable components, i.e., components derived from biosources. In particular, as provided in the first embodiment herein, a renewable fuel is provided comprised of (a) one or more low carbon esters derivable from ethanol, (b) one or more pentosan derivable furans, (c) one or more aromatic hydrocarbons derived from acetone or propyne, (d) one or more $C_6$-$C_8$ straight chain alkanes derivable from polysaccharides and (e) one or more bio-oils derived from plant germ. In addition, as provided by the fourteenth and fifteenth embodiment herein, the renewable fuel may contain triethanolamine, which provides lubricity. Amines have been known to increase lubricity in internal combustion engines; triethanolamine having such a property when used with the other renewable components.

With regards to component (a), i.e., low carbon number esters, it is preferable to utilize esters having a carbon number of 1-4, such as ethyl acetate, butyl acetate or propyl acetate. Most preferably, ethyl acetate is used, as ethyl acetate provides an increase in the fuel's vapor pressure, essential for cold weather operations. These low carbon number esters are derivable from ethanol, using processes such as direct reaction with acetic acid in the presence of sulfuric acid. Further, the acetic acid can be directly derived from ethanol, if desired. All of these components can be derived from kernel corn, switchgrass or other cellulosic or sugar based materials.

With regards to component (b), i.e., pentosan derivable furans, it is preferable to utilize substituted furans. Most preferably, 2-methyl furans are used. The pentosan derivable furans are derived from corn stalks, stalks of other grains, and potentially, grasses. Specific furans are used as octane and energy increasing components.

With regards to component (c), i.e., aromatic hydrocarbons, unlike conventional petroleum-based fuels, the present invention comprises aromatic hydrocarbons derived from acetone, a fully renewable source. Most preferably, the aromatic hydrocarbon is mesitylene. Mesitylene can conveniently be prepared by the trimerization of acetone or propyne; acetone can be readily prepared from biomass, and propyne can be extracted from natural gas. Mesitylene is preferred, since the acetone or propyne reaction "stops" at the trimer, which makes the conversion high due to lack of significant side-reactions. Mesitylene can be used as an octane and energy enhancing ingredient.

With regards to component (d), i.e., straight chain alkanes in the $C_4$ to $C_{10}$ range, the alkanes are derived from biomass, specifically polysaccharides derived from biomass. Straight chain alkanes have the lowest octane number of a given set of alkane isomers; the more branched the molecule, the smoother combusting (higher octane) the molecule exhibits when tested. Preferably $C_5$ to $C_9$ straight chain alkanes are utilized. Most preferably $C_6$ to $C_8$ straight chain alkanes are included in the fuel. These straight chain alkanes act as octane depressants within the fuel. Most preferably, the straight chain alkanes are one or more chosen from n-pentane, n-hexane, n-heptane, n-octane, and n-nonane.

Lower straight chain alkanes, such as n-pentane, n-butane, propane and below, have too low of a boiling point to be useful as a main component of the developed fuel. Higher straight chain alkanes, such as n-nonane, n-decane and above, have too high of a carbon-to-hydrogen molecule fraction (>0.444). This high fraction leads to incomplete combustion in heat engines and coking. Straight chain alkanes are used to suppress the octane of a given fuel, while maintaining a high energy content per unit volume. Higher alkanes can be used in diesel and jet turbine applications.

With regards to component (e), i.e., bio-oils derived from plant germ, these components may be derived from various plant sources. For example, the bio-oil may include soybean oil, rapeseed oil, canola oil or corn oil, palm oil, and combinations thereof. Most preferably, corn oil is utilized as the bio-oil component because of its enhancement of energy, fuel's physical properties, and lubricity properties. Corn oil is derived directly from the corn germ.

Further, optionally, as called for in the fourteenth embodiments herein, the renewable fuel of the present invention may additionally contain component (f), i.e., triethanolamine. The inclusion of triethanolamine in the renewable fuel provides the advantage of lubricity at low concentrations, as well as effective octane improvement due to the combustion inhibition properties of the nitrogen moiety. Triethanolamine can be derived from ammonia and ethylene, both of which can be conveniently produced from biomass.

It was unexpectedly discovered by the present inventors that, by combining the above components (a)-(f) in the weight ranges called for herein in the second and fifteenth embodiments herein, a completely non-petroleum-based fuel, fully derivable from renewable biomass sources, could be obtained. Further, it was discovered that the fuel components could be conveniently adjusted to produce an appropriate air to fuel ratio for application in a heat engine. In the case of aircraft engines, that value was 14.2 to 1, based on mass. Further, it was unexpectedly discovered that this renewable fuel can be formulated to have a very high octane, e.g., up to 160 MON, by varying the octane increasing ingredients, such as the furans, with the energy increasing components such as mesitylene and corn oil.

Alternatively, as called for in the present invention, the present inventors unexpectedly discovered that the renewable fuel of the present invention could be formulated to have a much lower octane rating, such as 84 MON, which can be, for example, utilized as an automotive fuel. In particular, a high energy, octane depressant (component (d)), such as n-heptane, can be added to the fuel to obtain a lower octane rated fuel for use in conventional automotive and aviation applications. Another method of formulating a lower octane fuel, known as "derating", includes the substitution of acetone or tetrahydrofuran or other low octane ingredients for the ethyl acetate, while increasing the energy content.

Representative examples of the renewable fuels (identified in the column labeled "Invention Formulation") of the present invention, which have been prepared in the laboratory, are shown below in Table 1.

TABLE 1

"Composition Matrix for Invented Formulations"

| Invention Formulation | Ethyl Acetate | 2-Methyl Furan | Mesitylene | n-Heptane | Corn Oil |
|---|---|---|---|---|---|
| High Octane AvGas | 17.5% | 17.5% | 60.0% | 0.0% | 5.0% |
| 100LL Replacement | 13.1% | 13.1% | 45.0% | 25.0% | 3.8% |
| Auto Gas | 9.0% | 10.0% | 36.0% | 40.0% | 5.0% |
| Turbine Fuel | 8.0% | 24.0% | 60.0% | 0.0% | 8.0% |
| Turbine Fuel 2 | 0.0% | 0.0% | 0.0% | 63.0% | 37.0% |
| Diesel Fuel | 0.0% | 0.0% | 0.0% | 63.0% | 37.0% |
| Rocket Fuel | 0.0% | 0.0% | 60.0% | 35.0% | 5.0% |

Preparation Example

4-Cycle Engine Fuel 17.5 grams of ethyl acetate were mixed with 17.5 grams of 2-methyl furan. 60 grams of mesitylene were then added, followed by 5 grams of corn oil, to form 100 grams of fuel of the present invention. The mixture was stirred until all components were dissolved. The resulting solution was then analyzed, and found to have an effective MON of 142, and an optimum mixture ratio of 14.2 based on mass. This fuel has been effectively demonstrated in low and high compression reciprocating aviation engines.

Test Examples

In order to determine the characteristics of the renewable engine fuel of the present invention (representative examples of which are described as "Invention Formulation" in Table 1 above), the present inventors prepared the following fuels of the present invention (denoted in Table 2 as "100 LL Replacement and High Octane AvGas), and conducted calorimetric tests thereof. In particular, calorimetry was conducted in a Parr combustion bomb. Octane measurements were done by variable compression ratio engine testing under more severe conditions to assess Motor Octane Number (MON).

Bulk calorimetry accurately determines the energy content (heat of combustion) of a given component or mixture. MON values were conducted by Intertek Caleb Brett® under the ASTM D2700M methodology.

Through thermophysical analysis and initial formulation, a series of four- and five-part mixtures according to the present invention, as shown in Table 2 below, were prepared, which have been shown through testing to be capable of directly replacing conventional 100 LL Aviation Fuel and conventional High Octane Aviation Fuel. The composition information for these fuels is found in Table 1.

Upon further testing in the laboratory, through the use of a bulk calorimeter, the present inventors have confirmed that the test results for the renewable fuel of the present invention (denoted as 100 LL Replacement in Tables 1 and 2) are comparable with the currently used 100 LL aviation fuel properties. The characteristics of these renewable fuels of the present invention, obtained through testing as described above, are shown in Table 2. Also shown in Table 2 are the physical and chemical properties for conventional 100 LL aviation fuel, for comparison, shown as the second column under "Current Fuel".

TABLE 2

"Comparison of Current 100LL Aviation Fuel and Invented Aviation Fuels"

| Characteristic | Units | Current Fuel | 100LL Replacement | High Octane AvGas |
|---|---|---|---|---|
| Motor Octane Number | | ≧101 | 107 | 142 |
| Net Heat of Combustion | kcal/cc | ≧7.49 | 7.96 | 7.99 |
| Air to Fuel Ratio | w/w | ≧14.00 | 15.13 | 14.20 |
| Average Empirical Formula | | $C_8H_{18}$ | $C_{9.1}H_{15}O_{0.7}$ | $C_{9.8}H_{14}O$ |
| Flame Temperature | ° K | ≧1906 | 2130 | 2140 |
| Density at 15° C. | kg/m$^3$ | ≧720.3 | 831.4 | 882.1 |
| Tetraethyl lead | gPb/l | 0.56 | 0 | 0 |
| Sulphur | % mass | ≦0.05 | 0 | 0 |
| Initial Boiling Point | ° C. | | 65 | 65 |
| Freezing Point | ° C. | ≦−58 | −66 | −58 |
| Final Boiling Point | ° C. | ≦168 | 165 | 165 |
| Hodges Vapor Pressure | kPa | 37 to 87 | 58 | 60 |
| Visible Lead Precipitate | mg/100 ml | ≦3 | 0 | 0 |
| Flame Color | | Orange | Orange | Orange |

The ethanol-based renewable fuels of the present invention can be derived from biosources, hence they are truly renewable. Furthermore, two of the components are directly synthesized from ethanol; which makes this technology complementary to existing and future ethanol plants. The raw materials for each of the components are polysaccharides or germ oils in some form; these have current and projected market prices.

Since there are fewer process steps and less severe conditions to synthesize these components from the sugars and oils, the ultimate per gallon costs promise to be equal to or less than current AvGas prices as of July 2007. Initial estimates project the manufactured cost per gallon to be on the order of $2.25 per gallon, versus 100 LL which ranges from $4.30 to $4.70 per gallon in the Midwest U.S. Thus, the present invention advantageously provides a cost effective, fully renewable, and high performing fuel capable of replacing currently used petroleum-based fuels.

Test Results for Synthetic 100 LL Octane Aviation Fuel

FIG. 1 shows the motor octane number for various concentrations of mesitylene in a binary mixture of isopentane and mesitylene. The data points represent test results obtained by Dixie Services, Tex, applying the test standards under ASTM D2700 motor octane number in lean configurations. Since the minimum motor octane number required for 100 LL octane aviation fuel is 99.5, it can be seen from FIG. 1 that all blends greater than about 70 wt % mesitylene meet that specification.

Figure 2:
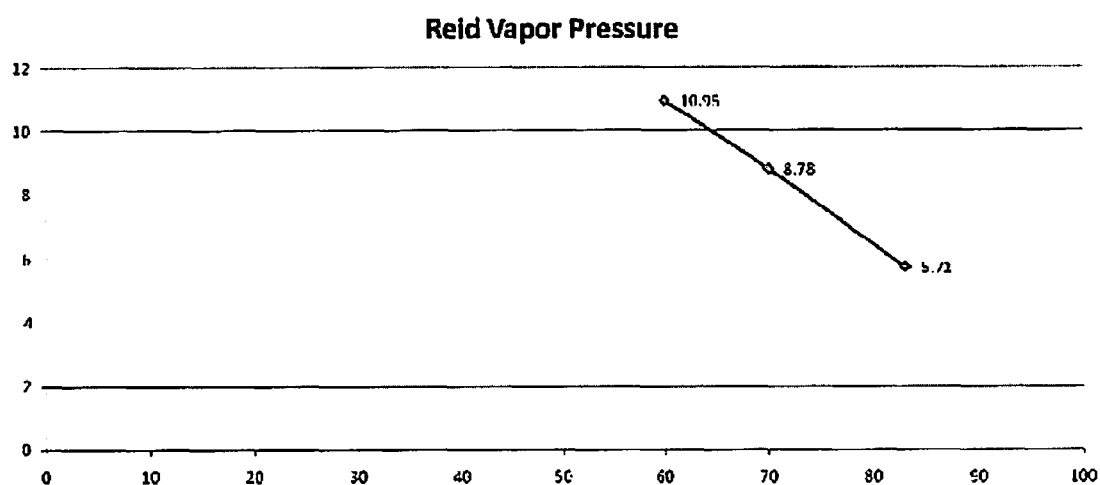
FIG. 2 is a graph of the Reid vapor pressure as a function of the wt % of mesitylene for the binary mixture of isopentane and mesitylene of the present invention.

FIG. 2 shows the Reid vapor pressure as a function of concentration (wt %) of mesitylene for a binary mixture of isopentane and mesitylene. These tests were conducted by Dixie Services Tex according to ASTM D5191. The 0% and 100% (pure chemicals) were not tested. Note that the specification for Reid vapor pressure of 100 LL octane aviation fuel is between 5.5 and 7.1 psi. It can be seen from FIG. 2 that mesitylene concentrations of from about 70-85 wt % meet that Reid vapor pressure requirement. Also, neither pure mesitylene nor pure isopentane meet that specification.

TABLE 3

| ASTM Method | Test | Mesitylene | Isopentane | Swift 702 | 100 spec |
|---|---|---|---|---|---|
| D2700 | Motor Octane Number | 136 | 90.3 | 104.9 | ≧99.5 |
| D909 | Supercharge ON | 170 | 92.3 | 133.0 | 130.0 |
| D5191 | Vapor Pressure | ≦5.5 | ≧7.1 | 5.7 | 5.5 to 7.1 |
| D2386 | Freezing Pt | −49 | −161 | −63 | ≦58 |
| D86 | 10% Distillation Pt. | 165 | 28 | 65 | ≦75 |
| D86 | End Distillation Pt. | 185 | 28 | 165 | ≦170 |

Table 3 above presents test results for six ASTM standards (methods) for pure mesitylene, pure isopentane, Swift 702 pure fuel (83 wt % of mesitylene and 17 wt % isopentane), and the ASTM standard (method) for 100 LL octane aviation fuel. Applicants unexpectedly discovered that adding isopentane to mesitylene increases the vapor pressure, lowers the freezing point, and lowers the 10% distillation point of mesitylene to within the ASTM standard as shown in Table 3. Applicants also unexpectedly discovered that adding mesitylene to isopentane to form a 100 octane aviation fuel raises the motor octane number of the isopentane, raises the supercharge octane number of isopentane, and lowers the vapor pressure of isopentane to within the ASTM D910 specification.

Although specific embodiments of the present invention have been disclosed herein, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

What is claimed is:

1. A synthetic 100 LL octane aviation fuel comprising:
(a) 70-85 wt % of sym-trimethyl benzene (mesitylene); and
(b) 15-30 wt % of isopentane,
wherein the fuel has a motor octane number of 99.5 or greater, and a Reid vapor pressure of from 5.5 to 7.1 psi.

* * * * *